(12) United States Patent
Giordano et al.

(10) Patent No.: US 11,992,397 B2
(45) Date of Patent: May 28, 2024

(54) HOLDER FOR HEART VALVE PROSTHESIS, A STORAGE ARRANGEMENT FOR A HEART VALVE PROSTHESIS, AND A CRIMPING KIT AND METHOD

(71) Applicant: Corcym S.r.l., Milan (IT)

(72) Inventors: Giovanni Giordano, Saluggia (IT); Monica Francesca Achiluzzi, Saluggia (IT)

(73) Assignee: Corcym S.r.l., Milan (IT)

( * ) Notice: Subject to any disclaimer, the term of this patent is extended or adjusted under 35 U.S.C. 154(b) by 752 days.

(21) Appl. No.: 17/057,511

(22) PCT Filed: May 23, 2018

(86) PCT No.: PCT/IB2018/053645
§ 371 (c)(1),
(2) Date: Nov. 20, 2020

(87) PCT Pub. No.: WO2019/224580
PCT Pub. Date: Nov. 28, 2019

(65) Prior Publication Data
US 2021/0196442 A1    Jul. 1, 2021

(51) Int. Cl.
*A61F 2/00* (2006.01)
*A61F 2/24* (2006.01)
*A61F 2/95* (2013.01)

(52) U.S. Cl.
CPC .......... *A61F 2/0095* (2013.01); *A61F 2/2418* (2013.01); *A61F 2/2427* (2013.01); *A61F 2/9524* (2020.05)

(58) Field of Classification Search
CPC .... A61F 2/9524; A61F 2/0095; A61F 2/2418; A61F 2/2427
See application file for complete search history.

(56) References Cited

U.S. PATENT DOCUMENTS 3,363,442 A    1/1968  Kennedy et al.
3,409,013 A   11/1968  Henry et al.
(Continued)

FOREIGN PATENT DOCUMENTS

DE        29911694 U1    8/1999
DE    102004019254 B3    7/2005
(Continued)

OTHER PUBLICATIONS

International Search Report and Written Opinion for International Application No. PCT/IB2018/053645, dated Mar. 28, 2019, 15 pages.

*Primary Examiner* — Christie Bahena
(74) *Attorney, Agent, or Firm* — Eversheds Sutherland (US) LLP; Christopher C. Bolten; Albert K. Heng

(57) ABSTRACT

The disclosure relates to a holder (1) for a heart valve prosthesis (100) including a radially contractible armature (102) and a prosthetic valve carried by said armature (102). The holder (1) includes an annular member (2) having a longitudinal axis (xl) and comprising a plurality of supporting formations (3), said supporting formations (3) protruding radially inwardly of said annular member (2), and a locking member (4) configured for coupling with said annular member (2). Each supporting formation (3) includes a coupling profile or feature (9) configured for engaging the armature (102) of a heart valve prosthesis (100). The coupling profile or feature (9) being configured to prevent the displacement of the armature (102) along said longitudinal axis and being configured to prevent rotation of the armature (102) around the longitudinal axis (X1), while leaving the armature (102) unconstrained in a radially inward direction. The locking member (4) is configured to removably mate with the annular member (2) to provide a radial constraint to
(Continued)

the armature in a radially inward direction at the supporting formations (3).

19 Claims, 11 Drawing Sheets

(56) References Cited

U.S. PATENT DOCUMENTS

| | | |
|---|---|---|
| 4,683,883 A | 8/1987 | Martin |
| 5,042,161 A | 8/1991 | Hodge |
| 5,360,014 A | 11/1994 | Sauter et al. |
| 5,489,296 A | 2/1996 | Love et al. |
| 5,522,884 A | 6/1996 | Wright |
| 5,560,487 A | 10/1996 | Starr |
| 5,669,919 A | 9/1997 | Sanders et al. |
| 5,672,169 A | 9/1997 | Verbeek |
| 5,693,066 A | 12/1997 | Rupp et al. |
| 5,698,307 A | 12/1997 | Levy |
| 5,776,187 A | 7/1998 | Krueger et al. |
| 5,800,531 A | 9/1998 | Cosgrove et al. |
| 5,810,873 A | 9/1998 | Morales |
| 5,814,096 A | 9/1998 | Lam et al. |
| 5,824,068 A | 10/1998 | Bugge |
| 5,885,228 A | 3/1999 | Rosenman et al. |
| 5,947,993 A | 9/1999 | Morales |
| 5,951,540 A | 9/1999 | Verbeek |
| 5,972,016 A | 10/1999 | Morales |
| 6,019,739 A | 2/2000 | Rhee et al. |
| 6,024,737 A | 2/2000 | Morales |
| 6,051,002 A | 4/2000 | Morales |
| 6,063,102 A | 5/2000 | Morales |
| 6,110,200 A | 8/2000 | Hinnenkamp |
| 6,202,272 B1 | 3/2001 | Jackson |
| 6,214,043 B1 | 4/2001 | Krueger et al. |
| 6,277,110 B1 | 8/2001 | Morales |
| 6,309,383 B1 | 10/2001 | Campbell et al. |
| 6,350,281 B1 | 2/2002 | Rhee |
| 6,352,547 B1 | 3/2002 | Brown et al. |
| 6,387,117 B1 | 5/2002 | Arnold, Jr. et al. |
| 6,402,780 B2 | 6/2002 | Williamson, IV et al. |
| 6,454,799 B1 | 9/2002 | Schreck |
| 6,481,262 B2 | 11/2002 | Ching et al. |
| 6,506,201 B2 | 1/2003 | Di Caprio et al. |
| 6,510,722 B1 | 1/2003 | Ching et al. |
| 6,598,307 B2 | 7/2003 | Love et al. |
| 6,629,350 B2 | 10/2003 | Motsenbocker |
| 6,678,962 B1 | 1/2004 | Love et al. |
| 6,726,713 B2 | 4/2004 | Schaldach et al. |
| 6,730,118 B2 | 5/2004 | Spenser et al. |
| 6,769,161 B2 | 8/2004 | Brown et al. |
| 6,846,324 B2 | 1/2005 | Stobie |
| 6,915,560 B2 | 7/2005 | Austin |
| 6,966,924 B2 | 11/2005 | Holmberg |
| 6,968,607 B2 | 11/2005 | Motsenbocker |
| 6,981,982 B2 | 1/2006 | Armstrong et al. |
| 6,988,881 B2 | 1/2006 | Motsenbocker et al. |
| 7,007,396 B2 | 3/2006 | Rudko et al. |
| 7,021,114 B2 | 4/2006 | Perreault |
| 7,069,794 B2 | 7/2006 | Motsenbocker et al. |
| 7,258,698 B2 | 8/2007 | Lemmon |
| 7,338,484 B2 | 3/2008 | Schoon et al. |
| 7,357,814 B2 | 4/2008 | Gabbay |
| 7,367,984 B2 | 5/2008 | Kulcinski et al. |
| 7,389,874 B2 | 6/2008 | Quest et al. |
| 7,427,291 B2 | 9/2008 | Liddicoat et al. |
| 8,006,535 B2 | 8/2011 | Righini et al. |
| 8,747,458 B2 | 6/2014 | Tuval et al. |
| 9,114,010 B2 | 8/2015 | Gaschino et al. |
| 9,585,752 B2 | 3/2017 | Chang et al. |
| 2001/0049558 A1 | 12/2001 | Liddicoat et al. |
| 2002/0035390 A1 | 3/2002 | Schaldach et al. |
| 2002/0042651 A1 | 4/2002 | Liddicoat et al. |
| 2002/0129820 A1 | 9/2002 | Ryan et al. |
| 2002/0198594 A1 | 12/2002 | Schreck |
| 2003/0114913 A1 | 6/2003 | Spenser et al. |
| 2003/0125805 A1 | 7/2003 | Johnson et al. |
| 2003/0192134 A1 | 10/2003 | Desenne et al. |
| 2003/0192164 A1 | 10/2003 | Austin |
| 2004/0039436 A1 | 2/2004 | Spenser et al. |
| 2004/0123437 A1 | 7/2004 | Kokish |
| 2004/0193259 A1 | 9/2004 | Gabbay |
| 2004/0225356 A1 | 11/2004 | Frater |
| 2005/0166389 A1 | 8/2005 | Perreault et al. |
| 2005/0197695 A1 | 9/2005 | Stacchino et al. |
| 2005/0197696 A1 | 9/2005 | Gomez Duran |
| 2005/0229670 A1 | 10/2005 | Perreault |
| 2005/0234537 A1 | 10/2005 | Edin |
| 2005/0240256 A1 | 10/2005 | Austin |
| 2005/0267529 A1 | 12/2005 | Crockett et al. |
| 2005/0283232 A1 | 12/2005 | Gabbay |
| 2006/0004469 A1 | 1/2006 | Sokel |
| 2006/0074486 A1 | 4/2006 | Liddicoat et al. |
| 2006/0178470 A1 | 8/2006 | Majolo et al. |
| 2006/0178740 A1 | 8/2006 | Stacchino et al. |
| 2006/0265855 A1 | 11/2006 | Stenzel |
| 2007/0027534 A1 | 2/2007 | Bergheim et al. |
| 2007/0056346 A1 | 3/2007 | Spenser et al. |
| 2007/0061009 A1 | 3/2007 | Spenser et al. |
| 2007/0100356 A1 | 5/2007 | Lucatero et al. |
| 2007/0162113 A1 | 7/2007 | Sharkawy et al. |
| 2007/0173861 A1 | 7/2007 | Strommer et al. |
| 2008/0071367 A1* | 3/2008 | Bergin .................. A61F 2/243 |
| | | 623/2.11 |
| 2008/0262603 A1 | 10/2008 | Giaquinta et al. |
| 2009/0018570 A1 | 1/2009 | Righini et al. |
| 2009/0054976 A1 | 2/2009 | Tuval et al. |
| 2009/0192603 A1 | 7/2009 | Ryan |
| 2010/0049313 A1 | 2/2010 | Alon et al. |
| 2010/0249661 A1 | 9/2010 | Righini et al. |
| 2010/0252470 A1 | 10/2010 | Ryan et al. |
| 2010/0262043 A1 | 10/2010 | Sauter et al. |
| 2010/0292779 A1 | 11/2010 | Straubinger et al. |
| 2012/0271398 A1 | 10/2012 | Essinger et al. |
| 2013/0261742 A1* | 10/2013 | Gaschino ............. A61F 2/0095 |
| | | 623/2.11 |
| 2014/0260097 A1 | 9/2014 | Avery et al. |
| 2015/0018938 A1 | 1/2015 | Von Segesser et al. |
| 2016/0128819 A1* | 5/2016 | Giordano ............. A61F 2/2427 |
| | | 623/2.11 |
| 2016/0354205 A1 | 12/2016 | Essinger et al. |

FOREIGN PATENT DOCUMENTS

| | | |
|---|---|---|
| DE | 102004019254 B8 | 11/2005 |
| DE | 202011000848 U1 | 6/2011 |
| EP | 0095970 A2 | 12/1983 |
| EP | 0778009 A2 | 6/1997 |
| EP | 0778009 B1 | 7/2002 |
| EP | 1353420 B1 | 3/2005 |
| EP | 2520251 A1 | 11/2012 |
| EP | 3034014 A2 | 6/2016 |
| GB | 2083362 A | 3/1982 |
| JP | H11332997 A | 12/1999 |
| JP | 2004154164 A | 6/2004 |
| WO | WO-9639942 A1 | 12/1996 |
| WO | WO-9724989 A1 | 7/1997 |
| WO | WO-9814138 A1 | 4/1998 |
| WO | WO-9953864 A1 | 10/1999 |
| WO | WO-9953866 A1 | 10/1999 |
| WO | WO-9955255 A1 | 11/1999 |
| WO | WO-0006052 A1 | 2/2000 |
| WO | WO-0021464 A1 | 4/2000 |
| WO | WO-0030565 A1 | 6/2000 |
| WO | WO-0119768 A2 | 3/2001 |
| WO | WO-0121076 A1 | 3/2001 |
| WO | WO-0121097 A2 | 3/2001 |
| WO | WO-0121103 A2 | 3/2001 |
| WO | WO-0121110 A1 | 3/2001 |
| WO | WO-0176510 A2 | 10/2001 |
| WO | WO-0176510 A8 | 1/2002 |
| WO | WO-0211646 A1 | 2/2002 |
| WO | WO-0121103 A9 | 10/2002 |
| WO | WO-02092257 A1 | 11/2002 |
| WO | WO-2005082578 A1 | 9/2005 |

(56) References Cited

FOREIGN PATENT DOCUMENTS

| WO | WO-2006088712 A1 | 8/2006 |
|---|---|---|
| WO | WO-2006117016 A1 | 11/2006 |
| WO | WO-2006127089 A1 | 11/2006 |
| WO | WO-2006136930 A1 | 12/2006 |
| WO | WO-2007030825 A2 | 3/2007 |
| WO | WO-2007030825 A3 | 6/2007 |
| WO | WO-2006007401 A3 | 1/2008 |
| WO | WO-2008008365 A2 | 1/2008 |
| WO | WO-0121097 A3 | 3/2008 |
| WO | WO-2008089365 A2 | 7/2008 |
| WO | WO-2009091509 A1 | 7/2009 |
| WO | WO-2009108942 A1 | 9/2009 |
| WO | WO-2010112608 A1 | 10/2010 |
| WO | WO-2010130789 A1 | 11/2010 |
| WO | WO-2012106491 A1 | 8/2012 |

\* cited by examiner

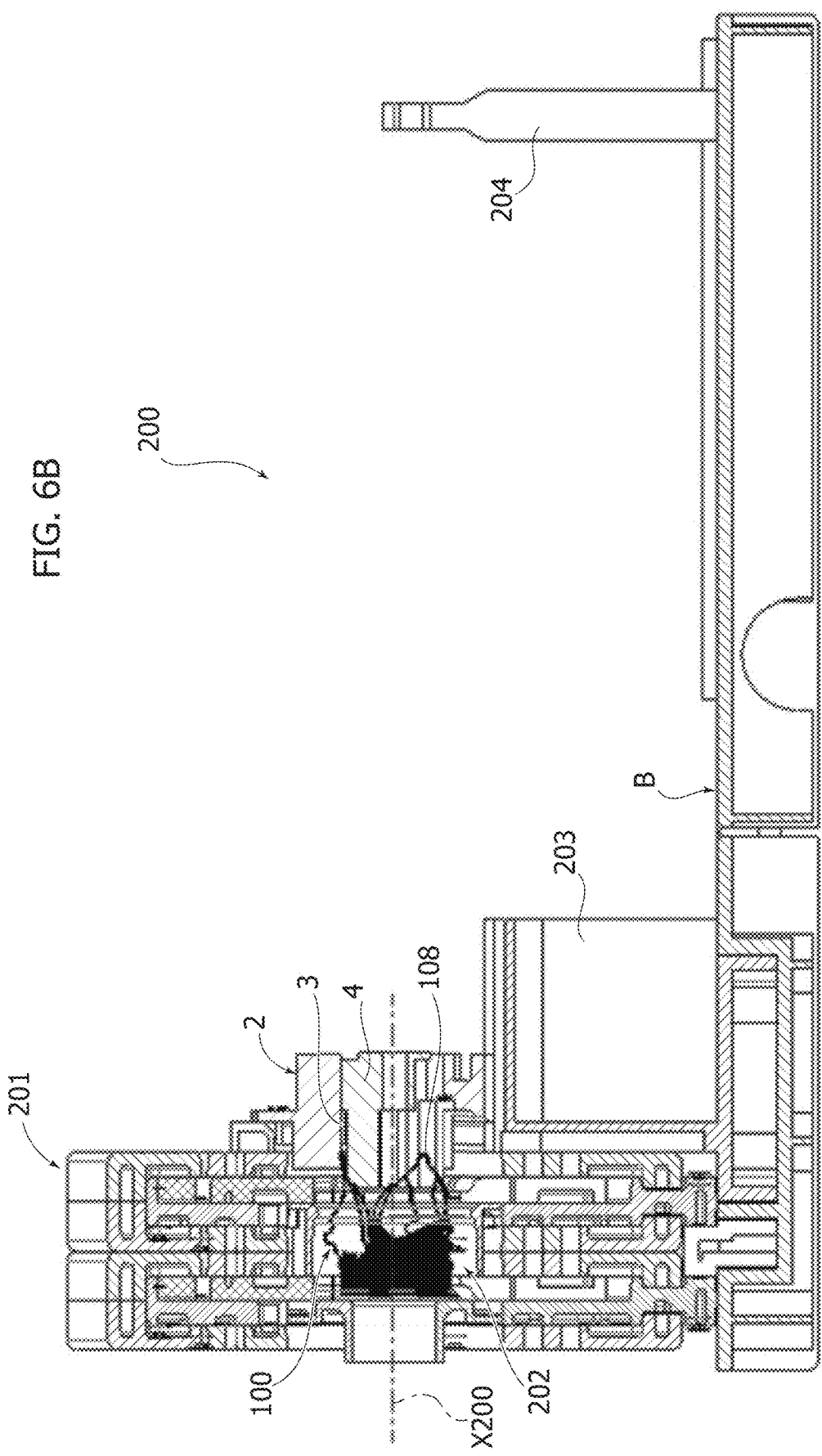

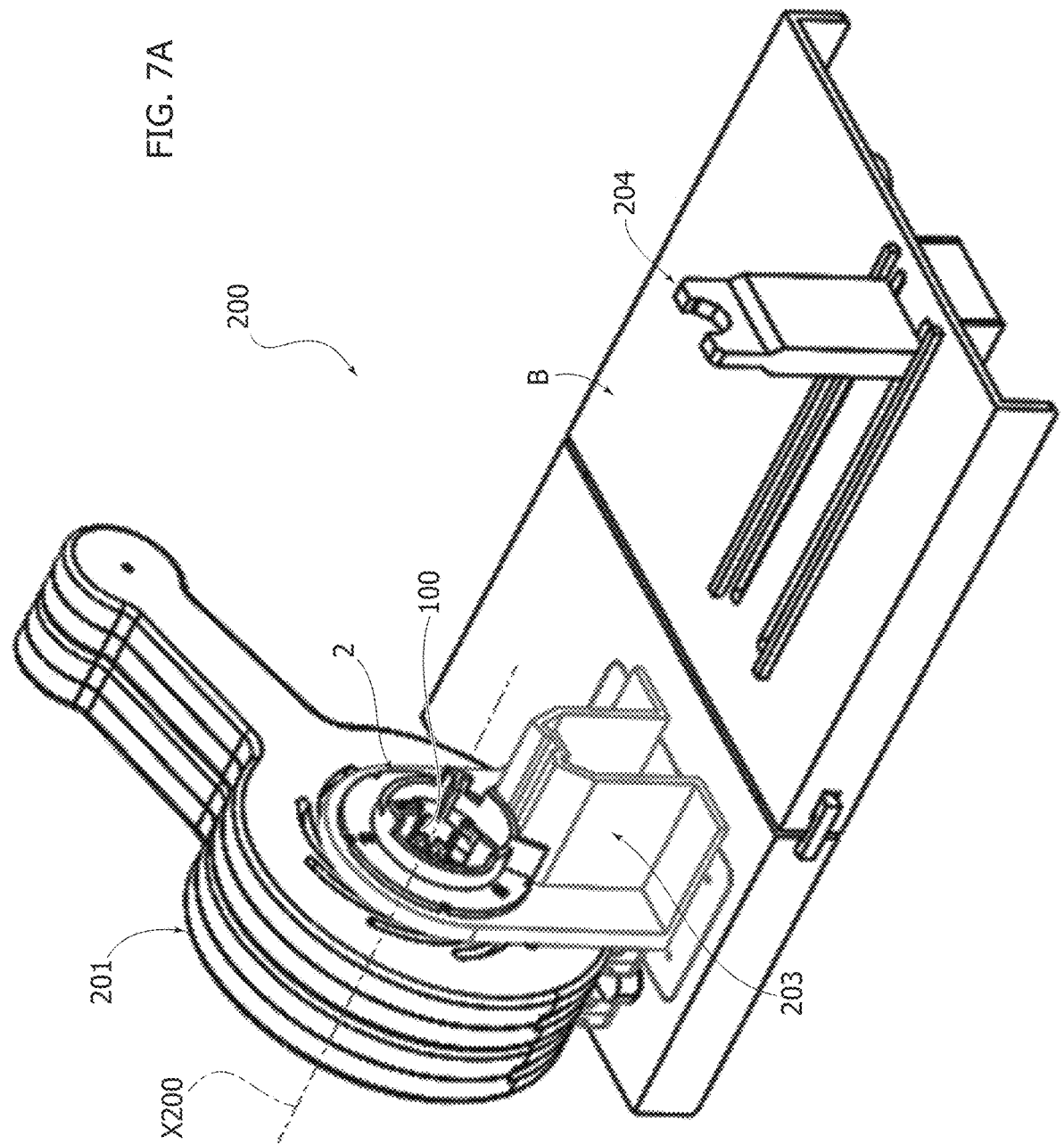

HOLDER FOR HEART VALVE PROSTHESIS, A STORAGE ARRANGEMENT FOR A HEART VALVE PROSTHESIS, AND A CRIMPING KIT AND METHOD

CROSS REFERENCE TO RELATED APPLICATIONS

This application is a national stage application of PCT/IB2018/053645 filed May 23, 2018, which is herein incorporated by reference in its entirety.

TECHNICAL FIELD

The disclosure relates to a holder for manipulating implantable medical devices such as a heart valve prosthesis including a radially contractible armature and a prosthetic heart valve carried by the armature, during a pre-operative procedure preceding the implantation of the heart valve prosthesis.

BACKGROUND

In the fields of heart valve surgery and interventional cardiology, easy handling of medical devices and the reduction of time required to perform surgical interventions and procedures are topics of interest for medical and technological research.

With reference to the implantation of expandable heart valve prostheses, such as for example sutureless valve prostheses, current practice provides that a heart valve prosthesis should be stored in a sterile environment in order to maintain its integrity and in order to prevent air from being trapped in the structure of the prosthesis.

Also, such prostheses may need to be crimped i.e. radially collapsed and coupled to a delivery instrument to be delivered to an implantation site, for example in a minimally invasive or percutaneous procedure.

Crimping an implantable medical device can present many important issues. While many crimping devices with different features have been devised to facilitate the crimping operation, such a step may remain rather delicate and complex to perform.

One of the challenges for the practitioner when crimping a heart valve prosthesis onto a delivery instrument, lies in achieving a desired position, in particular a desired angular position, of the implantable device on the crimping device. In various prior art devices, the delivery instruments are provided with angular indicia (for example markers which are intended to identify the commissures of an aortic or tricuspid valve) intended to aid the practitioner in correctly positioning the prosthesis at the implantation site.

Another challenge for the practitioner when implanting a heart valve prosthesis is the handling of the prosthesis from the storage facility (typically a so-called "jar" filled with a sterile solution for preservation) to the crimping instrument. Various current solutions require either multiple handling devices or even manual manipulation of the valve, which are both undesirable under the prospect of an easy and flawless valve positioning procedure.

SUMMARY

A first example of a holder for a heart valve prosthesis comprising a radially contractible armature and a prosthetic valve carried by said armature. The holder including an annular member having a longitudinal axis and comprising a plurality of supporting formations, said supporting formations protruding radially inwardly of said annular member, and a locking member configured for coupling with said annular member. Where, each supporting formation includes a coupling profile configured for engaging the armature of a heart valve prosthesis, the coupling profile being configured to prevent the displacement of the armature along said longitudinal axis and being configured to prevent rotation of the armature around the longitudinal axis, while leaving the armature unconstrained in a radially inward direction. The locking member is configured to removably mate with the annular member to provide a radial constraint to the armature in a radially inward direction at the supporting formations.

A second example according to the first example, wherein the annular member defines a lumen, the supporting formations protruding inwardly of said lumen.

A third example according to the first example, wherein the annular member includes an angular reference member configured for a sliding coupling with a fixed rectilinear guide, the angular reference member having a predetermined position relative to the supporting formations.

A fourth example according to the third example, wherein the angular reference member is provided on the periphery of said annular member and is configured as a slider member of a prismatic guide.

A fifth example according to the first example, wherein each coupling profile is a coupling interface for an arched strut comprising a cylindrical wall, and an arched track provided on the cylindrical wall and configured for receiving an arched strut, each coupling interface facing radially inwardly of said annular member. Where, at least one of said supporting formations includes a guide member for guiding said locking member upon mating to the annular member.

A sixth example according to the fifth example, wherein said guide member is configured for guiding said locking member in a direction parallel to said longitudinal axis.

A seventh example according to the fifth example, wherein said arched track includes a tooth protruding from the cylindrical wall and radially inwardly of the annular member, and a pair of arched protrusions arranged on opposite sides of said tooth.

An eighth example according to the seventh example, wherein said arched protrusions are spaced from one another in correspondence of said tooth.

A ninth example according to any of the previous examples, wherein said locking member is a hub member configured for mating to the annular member coaxially to the longitudinal axis thereof and including a cylindrical portion configured to settle among the supporting formations when the locking member is mated to the annular member.

A tenth example according to the ninth example, wherein the locking member further includes a guide portion, particularly provided on a rim, configured for slidably coupling with the guide members of the supporting formations.

An eleventh example according to the tenth example, wherein the guide portion is further configured to abut on an axial end portion of the supporting formations.

A twelfth example according to any of the previous examples, further including a heart valve prosthesis having a radially contractible armature and a prosthetic heart valve carried by said armature. The armature including an annular part, and a pattern of arched struts carried by said annular part. Said pattern of arched struts having proximal ends connected to said annular part, and distal ends spaced axially from the proximal ends and opposite said annular part (106).

Where, distal portions of the arched struts engage corresponding coupling profiles of the supporting formations.

A thirteenth example according to the twelfth example, wherein the distal portions of the arched struts are received in the arched tracks of the coupling profiles.

A fourteenth example of a holder for a heart valve prosthesis comprising a radially contractible armature and a prosthetic valve carried by said armature, the holder (1) including:
- an annular member having a longitudinal axis and comprising a plurality of supporting formations; and
- a locking member configured for coupling with said annular member, wherein:
- each supporting formation includes a coupling feature configured for engaging the armature of a heart valve prosthesis, so as to prevent the displacement of the armature along said longitudinal axis and rotation of the armature around the longitudinal axis, and
- the locking member is configured to removably mate with the annular member to provide a radial constraint to the armature in a radially inward direction at the supporting formations.

A fifteenth example according to the fourteenth example, wherein each coupling feature provides a coupling interface for an arched strut comprising:
- a cylindrical wall; and
- an arched track provided on the cylindrical wall and configured for receiving an arched strut,
- each coupling interface facing radially inwardly of said annular member.

A sixteenth example according to the fourteenth example, wherein at least one of said supporting formations includes a guide member for guiding said locking member upon mating to the annular member.

A seventeenth example according to the fourteenth example, wherein said locking member is a hub member configured for mating to the annular member coaxially to the longitudinal axis thereof and including a cylindrical portion configured to settle among the supporting formations when the locking member is mated to the annular member.

An eighteenth example according to the fourteenth example, wherein the annular member includes an angular reference member configured for a sliding coupling with a fixed rectilinear guide, the angular reference member having a predetermined position relative to the supporting formations.

A nineteenth example of a prosthetic heart valve storage kit including:
- a holder according to examples first to eighteenth;
- a heart valve prosthesis comprising a radially contractible armature and a prosthetic valve carried by said armature, the heart valve prosthesis being coupled to the holder at the supporting formations; and
- a container filled with a preservation solution, the holder being arranged in the container with the heart valve prosthesis immersed in the preservation solution.

A twentieth example of a crimping kit comprising:
- a crimping instrument with a crimping orifice having a longitudinal axis;
- a rectilinear guide oriented parallel to the longitudinal axis;
- a holder according to any of examples third to thirteenth or eighteenth; and
- a heart valve prosthesis comprising a radially contractible armature and a prosthetic valve carried by said armature, the heart valve prosthesis being coupled to the holder at the supporting formations, wherein the angular reference member of the holder is slidably coupled to said rectilinear guide to provide axial insertion of the prosthetic heart valve into the crimping orifice along the longitudinal axis thereof.

A twenty-first example of a method of crimping a heart valve prosthesis comprising a radially contractible armature and a prosthetic valve carried by said armature, the method comprising:
- providing a holder according to any of examples third to thirteenth or eighteenth, the holder further comprising a heart valve prosthesis including a radially contractible armature and a prosthetic valve carried by said armature, the heart valve prosthesis being coupled to the holder;
- providing a crimping kit according to the twentieth example;
- mating the angular reference member of the holder with the rectilinear guide of the crimping kit at a position distal from the crimping orifice, so as to present the heart valve prosthesis to the crimping orifice;
- advancing the holder along the rectilinear guide to insert the heart valve prosthesis into the crimping orifice;
- removing the locking member from the annular member of the holder; and
- crimping the heart valve prosthesis, thereby disengaging the armature from the supporting formations of the annular member.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE FIGURES

Various embodiments will now be described with reference to the attached figures, provided purely by way of non-limiting example, and wherein:

FIGS. 6A, 7A, and 8 are illustrative of a crimping kit, according to various embodiments, and are each representative of a respective step of a crimping method, according to various embodiments; and FIGS. 6B and 7B are longitudinal sectional views corresponding to FIGS. 6A and 7A, according to various embodiments.

Figure 1:
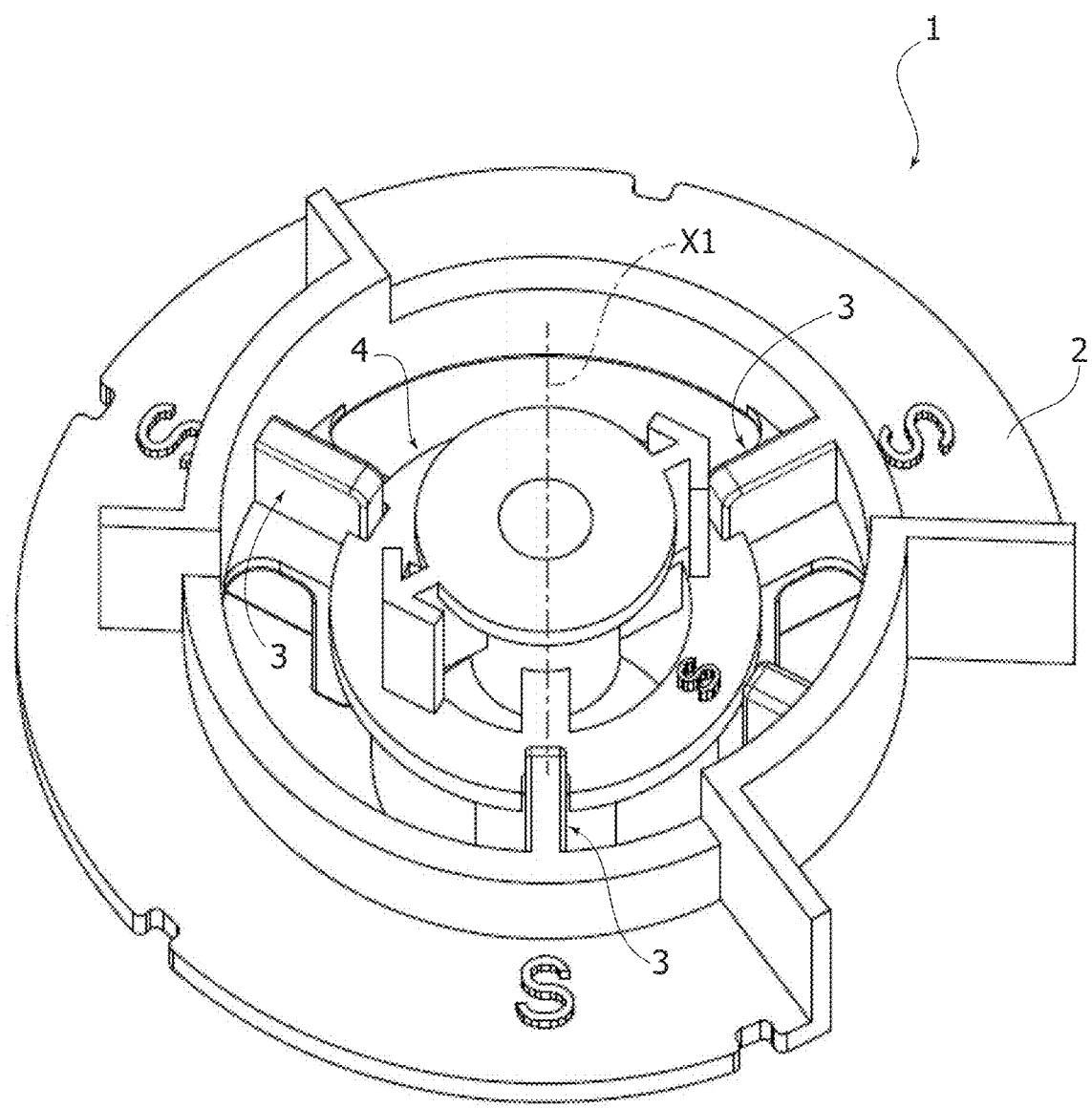
FIG. 1 is a perspective view of a holder, according to various embodiments.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

With reference to FIG. 1, reference number 1 designates a holder for a heart valve prosthesis according to various embodiments herein. The holder 1 may be used for supporting an implantable medical device such as a heart valve prosthesis including a radially contractible armature and a prosthetic valve carried by the armature. An exemplary heart valve prosthesis is disclosed, e.g., in PCT application no. PCT/IB2018/053640 filed on even date herewith and in the name of the same Applicant.

In embodiments, the holder 1 includes an annular member 2 having a longitudinal axis X1 (which also corresponds to the holder axis) and comprising a plurality of supporting formations 3, the supporting formations 3 protruding radially inwardly of the annular member 2, and a locking member 4 configured for coupling with the annular member 2.

Each supporting formation 3 includes a coupling feature configured for engaging the armature of a heart valve prosthesis supported by the holder 1, wherein the coupling feature is configured to limit the displacement of the armature along the longitudinal axis X1 while leaving the armature unconstrained in a radially inward direction. The locking member 4 is configured to removably mate with the annular member 2 to provide a radial constraint to the armature in a radially inward direction at the supporting formations 3.

In embodiments, the locking member 4 removably couples to the annular member 2, wherein coupling occurs through an axial sliding of the locking member 4 along the axis X1 and into the supporting formations 3, so that the locking member 4 is located among the supporting formations 3 and at least partially overlaps the same when mated to the annular member 2.

Figure 2A:
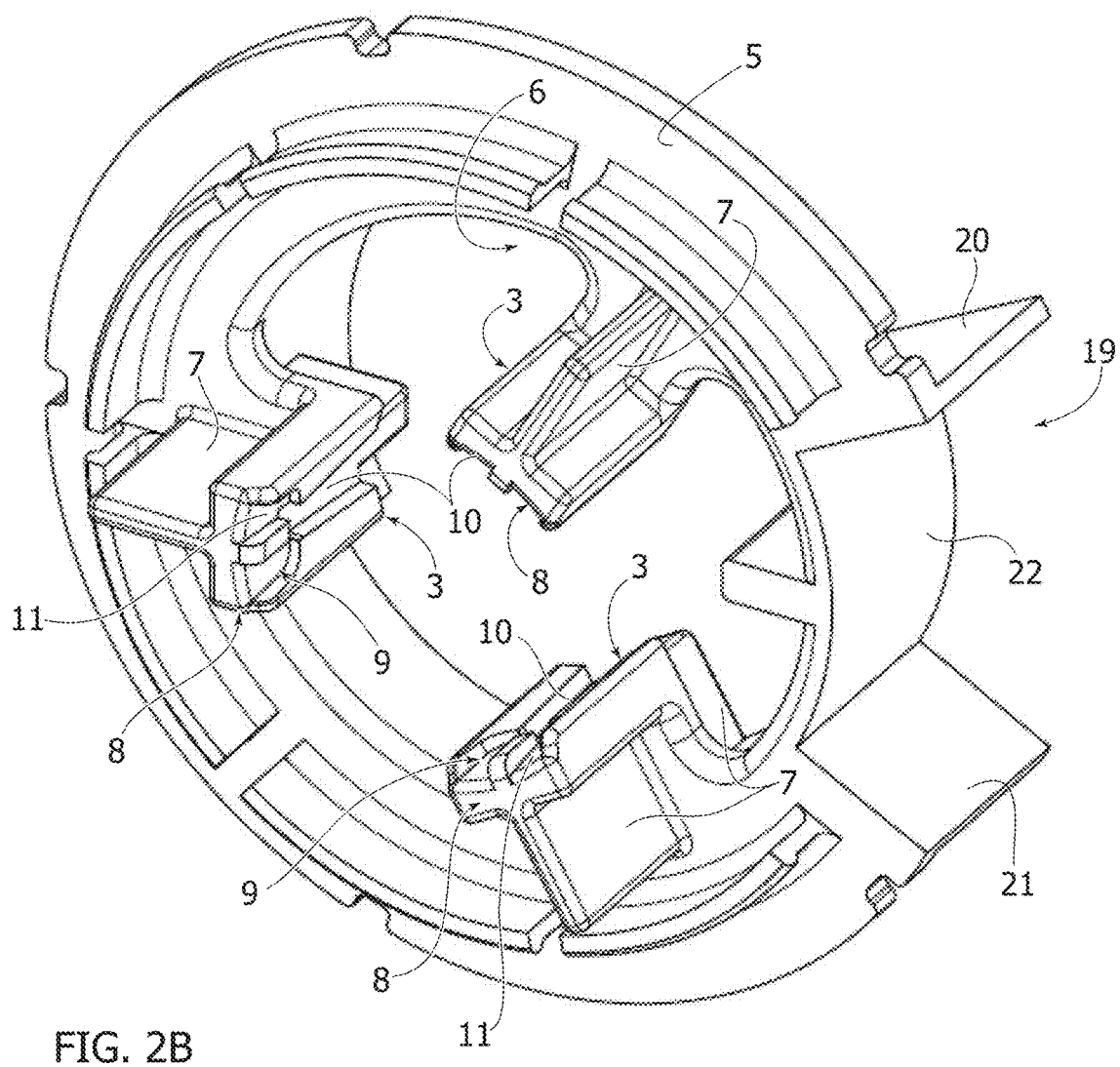
FIG. 2A is a perspective view of a first element of the holder of FIG. 1, according to various embodiments.

With reference to FIG. 2A, in embodiments the annular member 2 includes a peripheral rim 5 wherefrom the supporting formations 3 protrude radially inwardly in a spoke-like fashion. The peripheral rim 5 defines a lumen 6 for the prosthesis, wherein the supporting formations 3 protrude into the lumen 6.

The number and location of the supporting formations 3 may generally depend on the specific features of the heart valve prosthesis to be coupled to the holder 1. In embodiments shown in the figures, the supporting formations are in the number of three with even angular offset (120 degrees), bearing witness to the holder 1 being configured for coupling to the armature of an aortic heart valve prosthesis.

Figure 4A:
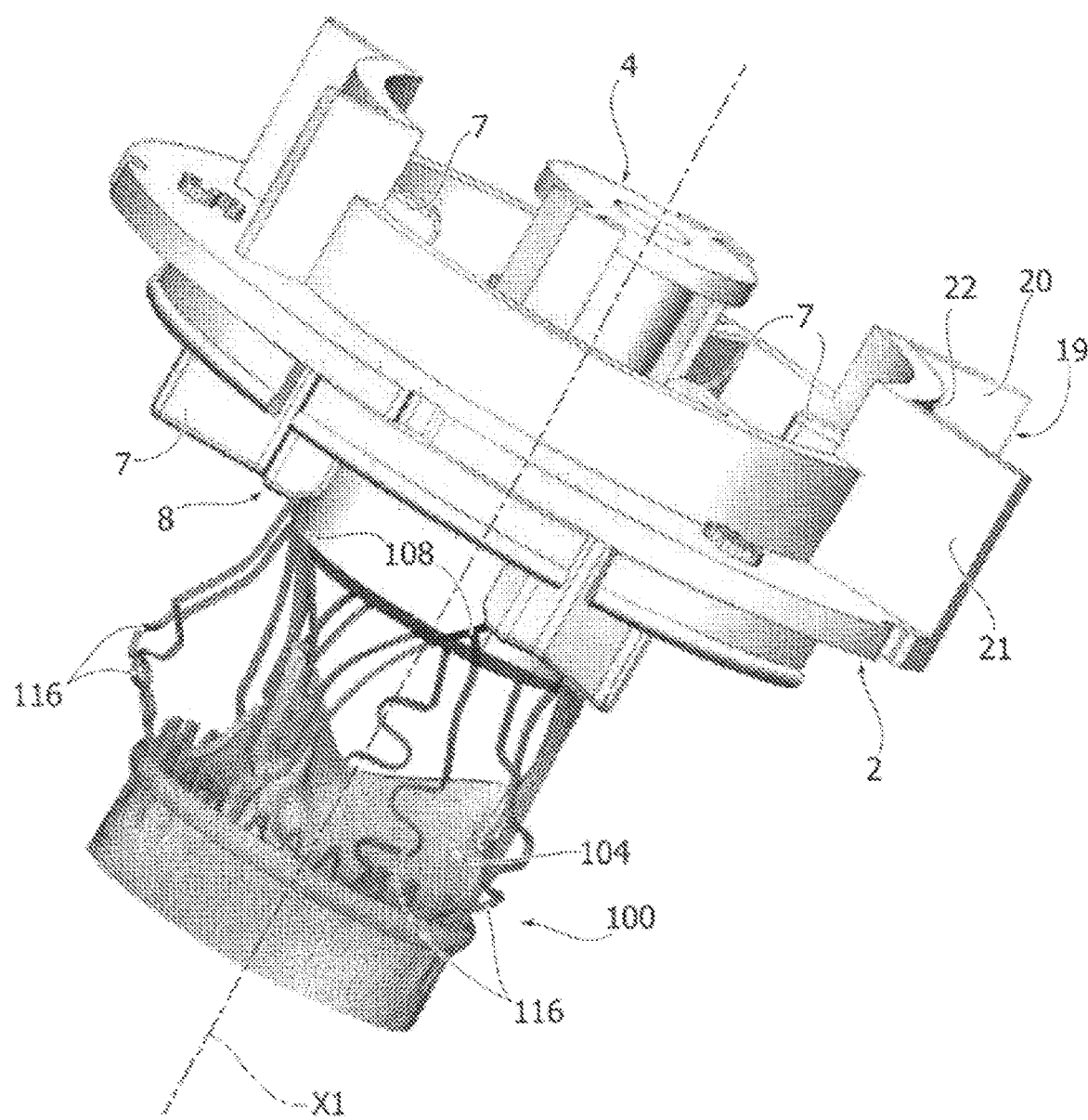
FIG. 4A is a perspective view of the holder of FIG. 1 with a heart valve prosthesis coupled thereto, according to various embodiments.
Figure 4B:
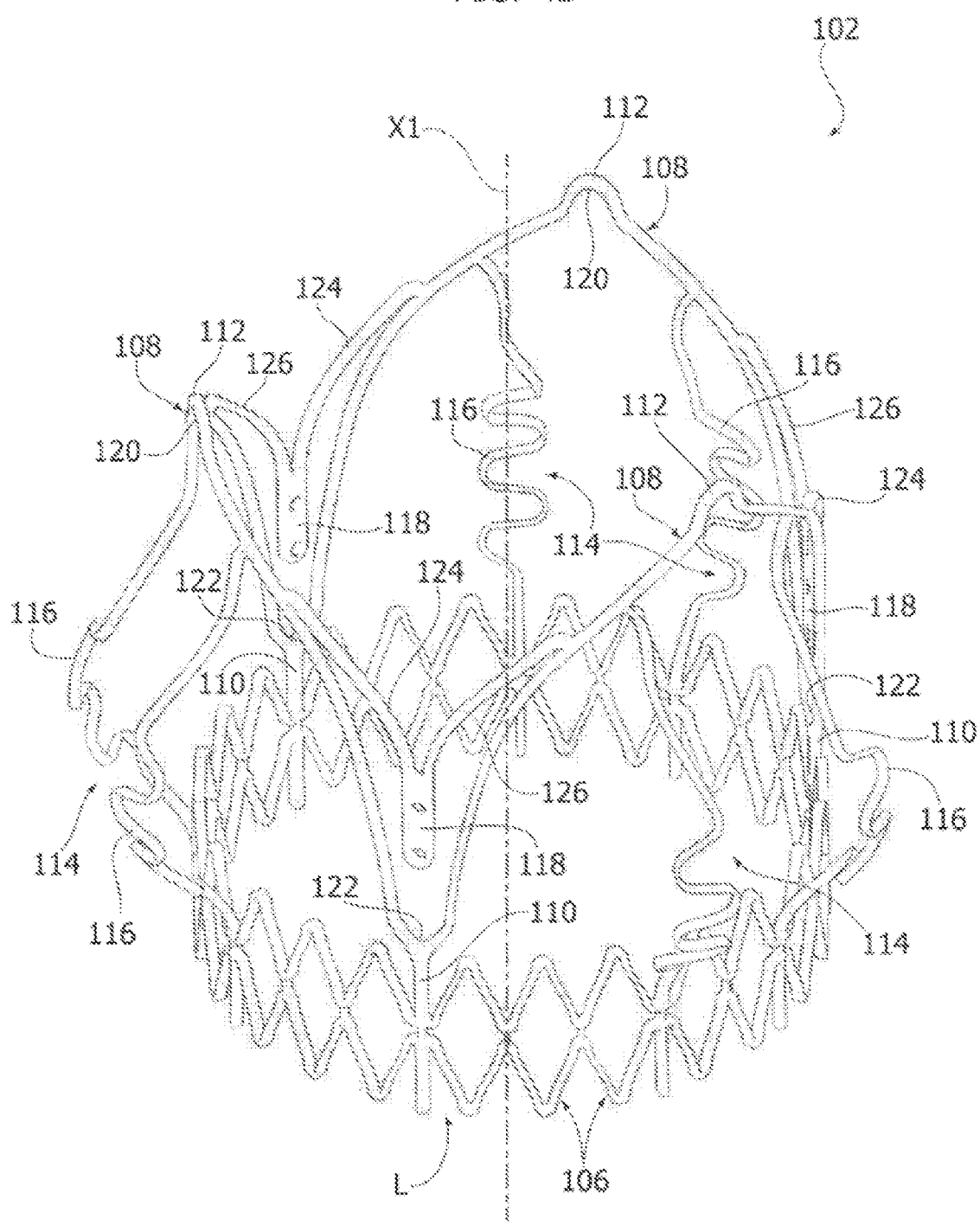
FIG. 4B is a perspective view of an exemplary armature of the heart valve prosthesis of FIG. 4A, according to various embodiments.

Embodiments of such a prosthesis are visible in FIG. 4B associated to reference number 100. The heart valve prosthesis 100 includes an armature 102 for anchorage of the valve prosthesis at an implantation site. The armature 102 defines a lumen for the passage of the blood flow and has a longitudinal axis X1.

The prosthesis 100 also includes a set of prosthetic valve leaflets 104 supported by the armature 102 and configured to move, under the action of blood flow, which has a main flow direction roughly corresponding to that of the axis X1, in a radially divaricated condition to enable the flow of blood through the lumen in a first direction, and in a radially contracted condition, in which the valve leaflets 104 cooperate with one another and block the flow of blood through the prosthesis 1 in the direction opposite the first direction. This is commonly referred to as leaflet coaptation.

The prosthetic leaflets 104 may be in any number compatible with operation as a replacement heart valve. In some embodiments, the set includes a pair of leaflets. In some embodiments, such as that shown in the figures, the set includes three prosthetic valve leaflets 104 (e.g. for an aortic valve prosthesis). In other embodiments, the set may include four leaflets 104.

The armature 102 includes an annular part 106, and a pattern of arched struts 108 carried by the annular part 106. The annular part 106 has a structure which can expand from a radially contracted condition, associated to delivery of the prosthesis to implantation site, to a radially expanded condition wherein the prosthesis is withheld at the implantation site. In embodiments, the annular part may have a mesh structure including an annular pattern of multiple strut clusters (cells) having polygonal shape (hexagonal, rhomboidal, etc.).

In embodiments, the annular part is covered by a cuff such as the sealing cuff SC to provide sealing at the implantation site, the cuff being arranged outside of the lumen of the armature 102. Advantageously, the cuff may be sewn or stitched to the annular part 106.

As said, depending on the technique used to manufacture the valvular sleeve, wherein the cuff SC may be integral with the set of prosthetic valve leaflets 104.

The pattern of arched struts 108 includes proximal ends 110 connected to the annular part 106, and distal ends 112 spaced axially from the proximal ends 110 and arranged at an end of the armature 102 opposite the annular part 106. In embodiments, the distal ends 112 coincide with distal ends of the armature 102, and in embodiments where the distal end of the armature 102 coincides with a distal end of the prosthesis 100 as a whole, the distal ends 112 coincide with a distal end of the prosthesis as well.

The armature 102 further includes a plurality of sets 114 of anchoring formations 116 configured to protrude radially outwardly of the annular part 106, each set 114 being supported by at least one of the annular part 106 and a corresponding arched strut 108, and a plurality of support posts 118, each supported by adjacent arched struts 108. Wherein the sets 114 of anchoring formations 116 alternate with the support posts 118 around the longitudinal axis X1. In embodiments the support posts 118 are cantilevered to adjacent arched struts 108 and are configured as fixing locations for the prosthetic valve, specifically for the pleat formations PF at the commissural points of the valve.

Each arched strut 108 extends from a first proximal end 110, to a distal end 112, then to a second proximal end 110 in a valley-peak-valley sequence, wherein valleys are located at the proximal ends 110, and peaks are located at the distal ends 112. In embodiments the pattern of arched struts includes three adjacent and preferably identical arched struts 108 (such as in the figures).

The pattern of arched struts 108 includes distal portions 120 located at the distal ends 112, and inter-strut portions 122 located at the proximal ends 110. The distal portions 120 may be shaped so as to provide a marked local variation in the shape of the strut, for example by exhibiting a C-shape as shown in the figure. The distal portions 120 may provide coupling locations for other devices such as a valve holder or a hub of a carrier portion of a delivery catheter. In other embodiments, the distal portions 120 may be provided as closed-loop structures such as eyes or eyelets.

In embodiments, the inter-strut portions 122 are essentially V-shaped and are defined by the roots of the adjacent arched struts departing from the same proximal end 110. In embodiments, the inter strut portions 122 may exhibit a Y-shape such as, for instance, that shown in the figure wherein each inter-strut portion 122 extends through the mesh of the annular part 106. Alternatively, a U-shape may be envisaged for the inter-strut portions 122. In embodiments, the mesh of the annular part 106 is provided as a sequence of rhomboidal strut clusters (cells) sequentially connected to each other at endpoints of a diagonal line (typically the shortest diagonal) and exhibiting accordingly an identical circular pattern of free ends on opposite sides of a circumference extending through the sequence of the connection points. The Y-shaped inter-strut portion 122 is thus integrally formed at a selected connection point between two adjacent rhomboidal strut clusters, and may extend no further than the proximal end of the armature 102.

The support posts 118 are angularly arranged at an inter-strut location, i.e. a circumferential location arranged at an area where an inter-strut portion 122 (as well as a proximal end 110 shared by two adjacent arched struts 108) is provided. The support posts may be provided as cantilevered to both the adjacent arched struts 108 intervening at an inter-strut portion 122 via a first and a second cantilever struts 124, 126, each connected to a corresponding one of said adjacent arched struts 108 as shown in the figures. The cantilever struts 124, 126 merge into each corresponding post 118 starting from locations on respective arched strut 108 approximately halfway through the portion of the arched strut 108 extending from a proximal end 110 to a distal end 112. The connection points at which the Y-shaped or U-shaped inter-strut portion 122 is formed may be chosen so that the same portions are evenly spaced (angular-wise) around the axis X1. The same applies to the support posts 118, which may be arranged so as to be evenly spaced (angular-wise) around the axis X1.

In embodiments shown in the figure, the armature 102 comprises three arched struts 108, three posts 118 spaced 120° around the axis X1, and three sets 114, so that the sequence around the axis X1 is post 118—set 114—post 118—set 114—post 118—set 114 (in this sense, even the struts 108 and the sets 114 do follow a 120 degree-like distribution). In embodiments the three sets 114 include each a pair of anchoring formations 116, wherein each set 114 (and accordingly each anchoring formation 116) extends bridge-wise between the annular part 106 and the corresponding arched strut 108.

With reference again to FIG. 2A, in embodiments, each supporting formation includes a radial tab member 7 and a circumferential tab member 8 which is arranged at a radially inward end of the tab member 7. In such embodiments, the circumferential tab member 8 may be generally orthogonal to the tab member 7. In embodiments, the circumferential tab member 8 carries the coupling feature of the supporting formation 3, wherein the coupling feature is generally indicated as 9 in the figures. In embodiments, the coupling feature 9 may be a coupling profile. Owing to the location on the tabs 8, each coupling profile or feature faces radially inwardly of the annular member 2. In embodiments, the coupling profile 9 is a recessed profile and is configured for receiving a portion—such as a strut—of the armature of the prosthesis to at least partially secure the prosthesis to the holder.

Figure 2B:
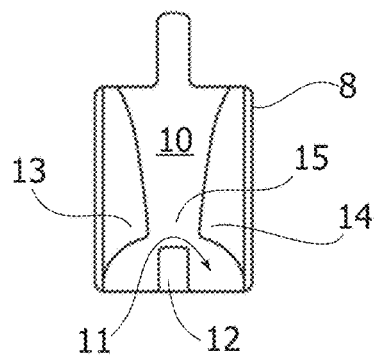
FIG. 2B is a view of a portion of the element of FIG. 2A, according to various embodiments.

In embodiments, each coupling profile 9 is a coupling interface comprising a cylindrical wall 10, which may be a radially innermost wall of the tab 8, an arched track 11 (FIG. 2B) provided on the cylindrical wall 10 and configured for receiving an arched strut 108 of the prosthesis 100, particularly a distal portion 120 thereof. In embodiments, the arched track 11 may receive any arched strut of a valve armature, and not necessarily those in the prosthesis 100. In embodiments, the arched track 11 is a recessed track.

The arched track (FIG. 2B) may include a tooth protruding from the cylindrical wall 10 radially inwardly of the annular member 2 (i.e. protruding into the lumen 6), and a pair of arched protrusions 13, 14 arranged on opposite sides of the tooth 12 and likewise protruding radially inwardly of the annular member 2.

In embodiments, the arched protrusions 13, 14 are spaced from one another in correspondence of the tooth 12 so as to provide a gap 15 therebetween. The gap 15 may serve as an additional coupling location to the arched track 11, especially when the arched strut of the prosthesis armature exhibits a hairpin-like shape that is able to penetrate (in a snap-fit fashion) through the interspace 15.

It should be noted, however, that depending on specific coupling requirements the coupling profiles may be provided as reliefs instead of recesses. In these embodiments, the reliefs couple with matching features of the armature of the heart valve prosthesis radially outwardly of the same. The mesh of radially contractible/expandable annular portion of the armature maybe an example of such matching features.

With combined reference to FIGS. 2A, 4A and 4B, in embodiments the prosthesis 100 (this applies to any prosthesis having a contractible armature featuring arched struts including arched or looped portions of the armature mesh) is coupled to the holder 1 so that the arched struts 108—and particularly the distal portions 120 thereof—are received in the arched track astride of the tooth 12. As a result, the axial displacement of the armature 102 is limited or substantially prevented, any rotational movement around the axis X1 is likewise prevented (thus providing a predetermined angular orientation of the prosthesis 100 relative to the holder 1), while radial displacement inwardly of the annular member 2 (i.e. inwardly of the lumen 6) remains fully allowed, as no radial constraint is provided by the supporting formations 3 relative to contraction of the armature 102. The locking member 4 is then inserted axially into the lumen 6 so as to settle among the supporting formations 3 with the armature of the prosthesis 100 located between the supporting formations 2 and the locking member 4.

In embodiments at least one—and preferably all—of the supporting formations includes a guide member for guiding the locking member 4 upon coupling to the annular member 2. These guide members may be provided, in embodiments such as that depicted in the figures, by the very radial tabs 7 which can act as rectilinear guides for the locking member 4, which may be provided with a correspondingly mating profile to the tabs 7. In other embodiments the guide member may be a member separate from the supporting formations, especially in those embodiments wherein the guide members are grouped in a pattern located on the rim 5 of the annular member in a position angularly offset from the pattern of supporting formations 3.

Whatever the embodiments, the guide members on the annular element are configured for guiding the locking member 4 in a direction parallel to the longitudinal axis X1.

Figure 3:
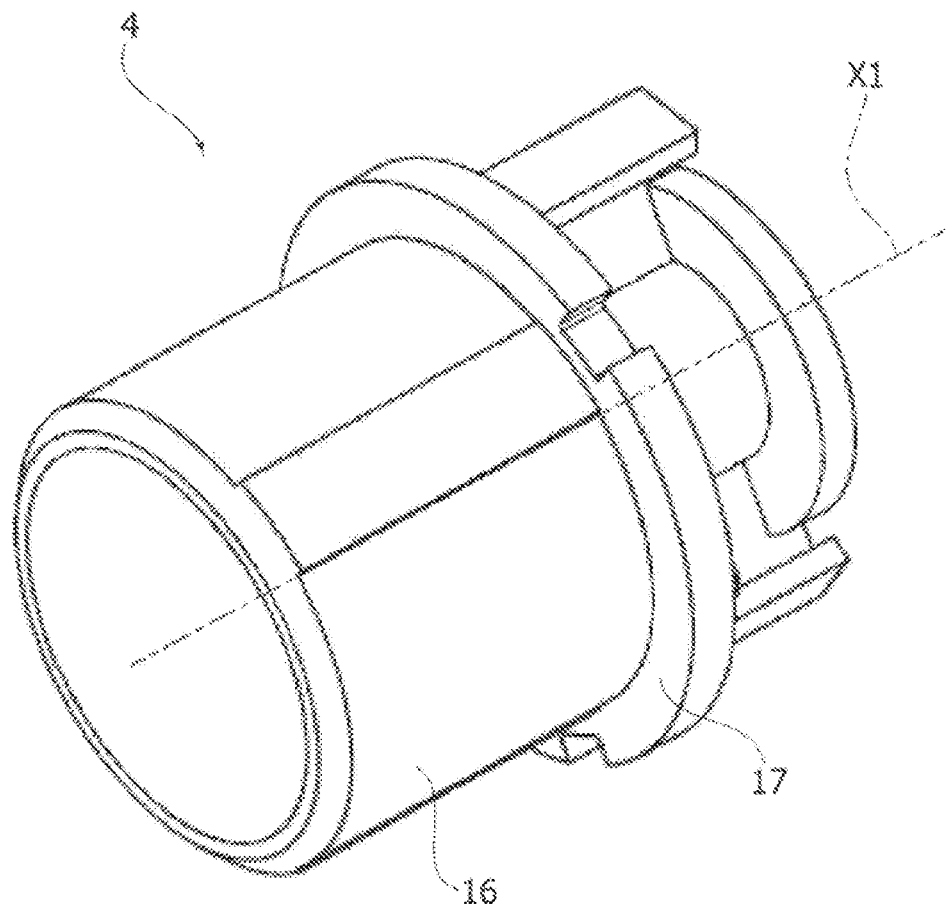
FIG. 3 is a perspective view of a second element of the holder of FIG. 1, according to various embodiments.

In embodiments (FIG. 3) the locking member 4 is provided as a hub member configured for mating to the annular member 2 coaxially to the longitudinal axis X1 thereof and including a cylindrical portion 16 configured to settle among the supporting formations 3 to provide a radial constraint to the armature of the prosthesis 100, particularly a radial constraint inwardly of the annular member 2. In embodiments, the locking member 4 provides a radial locking action against contraction of the prosthesis: being the latter axially and rotationally locked by the supporting formations 3, and likewise radially locked by the same formations relative to the expansion of the armature 102, the sole degree of freedom not taken away by the annular member 2 consists of the radial contraction of the armature 102. In this sense, the positioning of the locking member 4 with the hub portion 16 among the supporting formations 3 takes away this last degree of freedom as the armature gets sandwiched between the supporting formations and the hub portion of the locking member 4.

In embodiments the locking member 4 may further include a guide portion, particularly provided on a rim 17, which configured for slidably coupling with the guide members of the supporting formations 3, particularly with the tabs 7 the rim 17 may include in one embodiments a plurality of notches configured for mating with the radial tabs 7 to provide a sliding coupling therewith.

Additionally, in embodiments the rim 17 is configured to abut on an axial end portion of the supporting formations 3, particularly onto the tabs 8, to limit the penetration of the locking member 4 among the formations 3 and correctly position the locking member relative to the same.

In embodiments, the annular member 2 includes an angular reference member 19 configured for a sliding coupling with a fixed rectilinear guide. The angular reference member 19 has a predetermined angular position relative to the supporting formations 3, which in turn have an arrangement specific to the structure of the prosthesis they carry (hence a predetermined angular position relative to the prosthesis itself, as per the foregoing description). In this way the angular reference member 19 is univocally representative of the angular orientation of the prosthesis around the axis X1.

In embodiments, the angular reference member 19 is provided on the periphery of the annular member 2, particularly as apportion of the rim 5, and is configured as a slider member of a prismatic guide. In such embodiments, the angular reference member 19 includes two side radial tabs 20, 21 and a cylindrical wall 22 located between the tabs 20, 21. In other embodiments, the angular reference members—while maintaining the slider features—may be provided as a triangular or otherwise polygonal notch on the rim 5.

Figure 5:
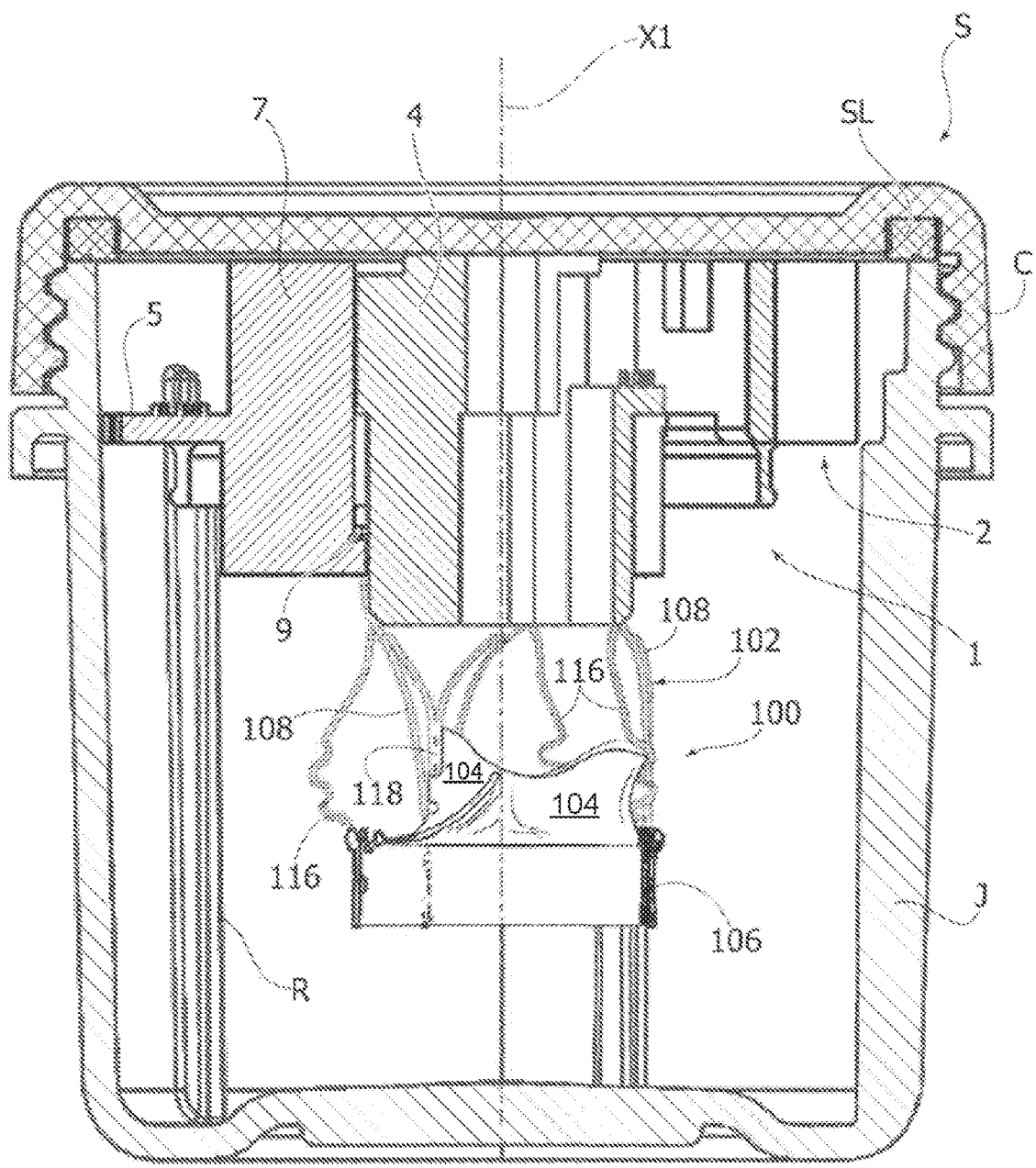
FIG. 5 is a cross sectional view of a storage kit, according to various embodiments.
Figure 6A:
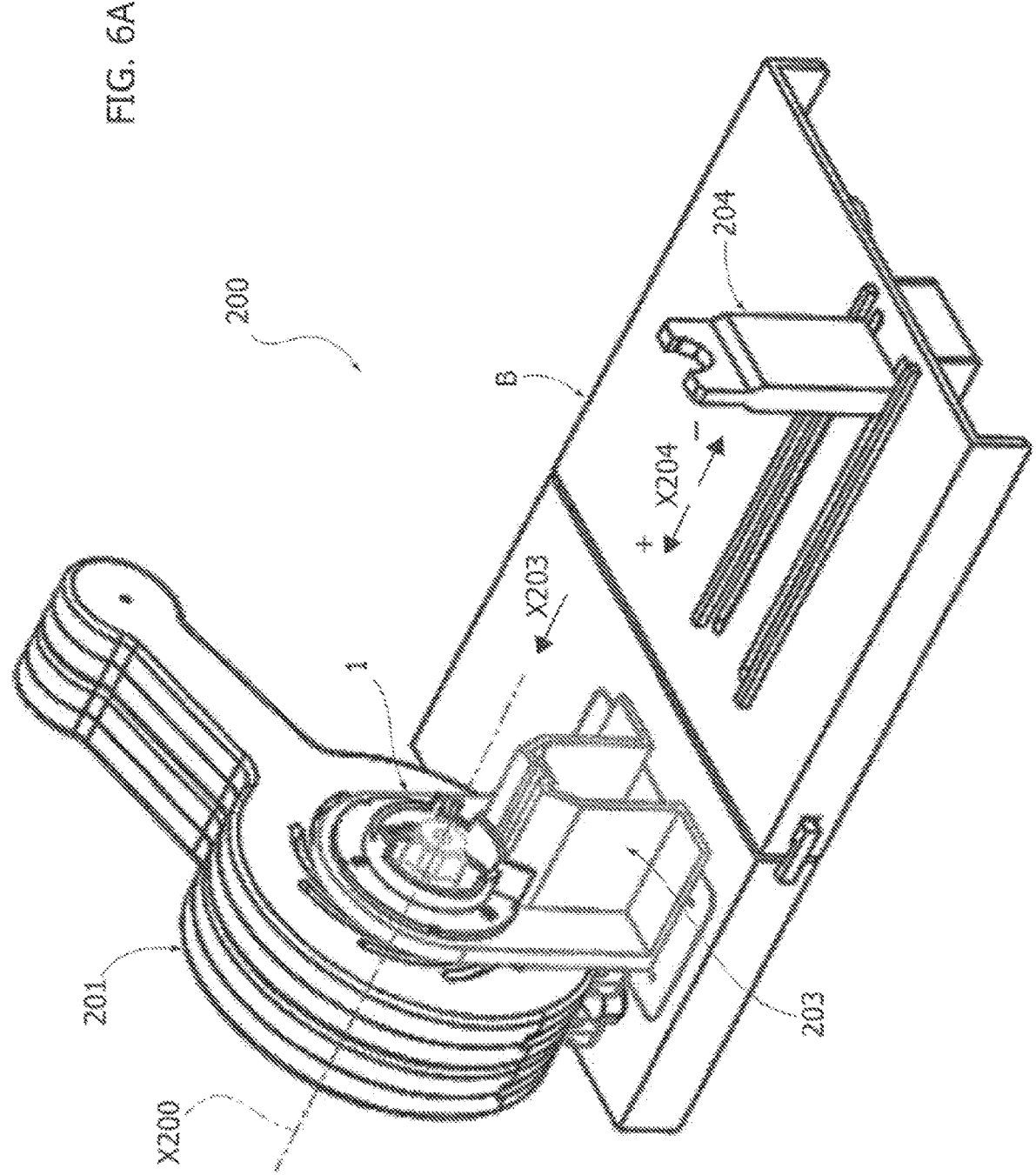
Figure 7B:
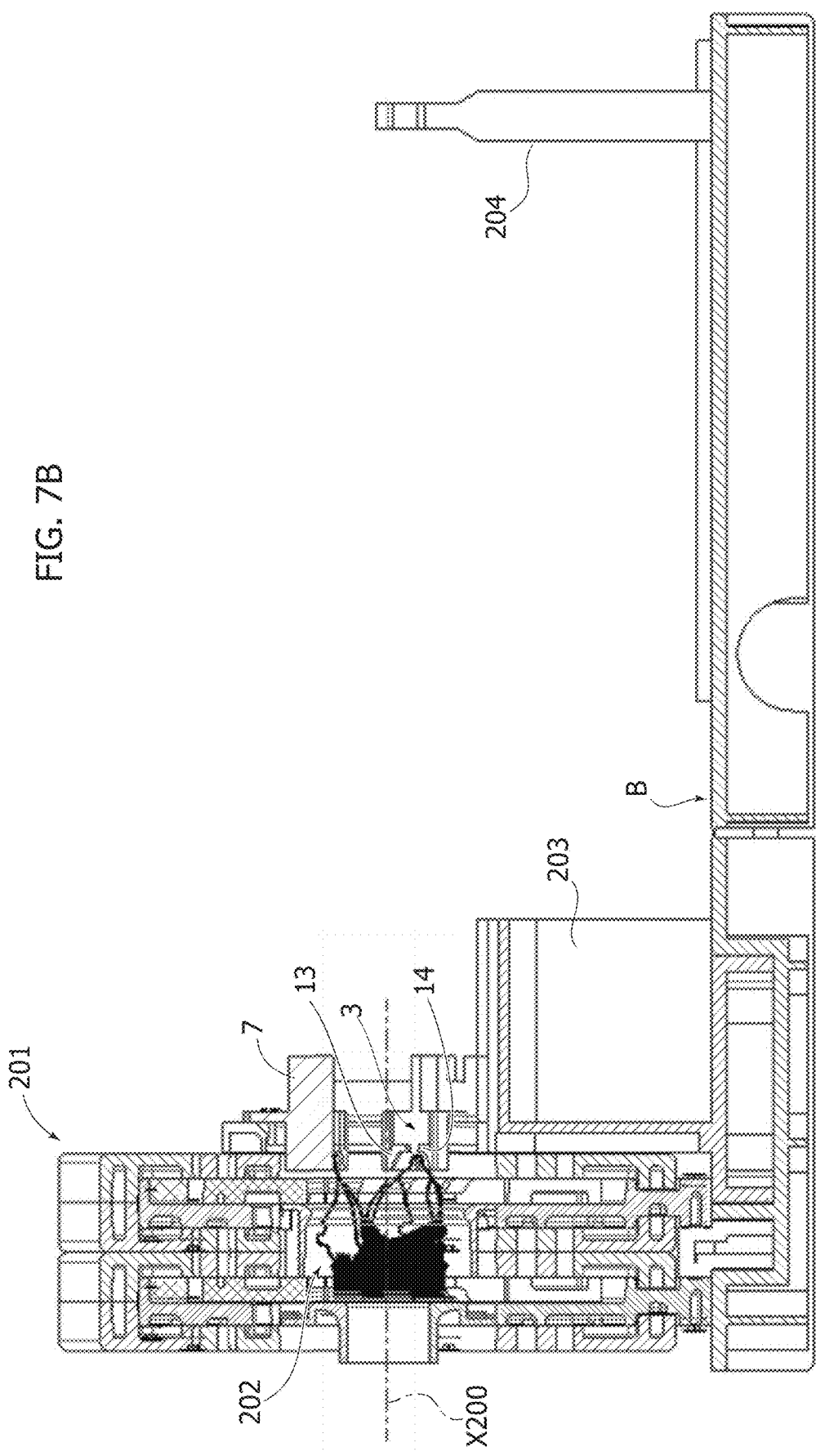

With reference to FIG. 5, in embodiments the holder 100 may be part of a storage kit S for a heart valve prosthesis 100 comprising a radially contractible armature (such as the armature 102) and a prosthetic valve carried by said armature.

In embodiments the storage kit S comprises the holder 1 and the prosthesis 100 coupled to the holder 1, i.e. coupled to the supporting formations 3 so to be axially and rotationally locked by the annular member 2, and furthermore radially locked both by the annular member 2 and the locking member 4.

In embodiments the storage kit S further comprises a container J (so called "jar") filled with a preservation solution and closed by a cap C with the interposition of a seal SL.

The holder 1 with the prosthesis 100 attached thereto is arranged in the container J with the heart valve prosthesis 100 immersed in the preservation solution. In embodiments the interior of the container J is provided with axial ribs R configured to engage notches on the periphery of the rim 5 to guide the holder into the container J and held it against rotation, as well as to set the axial position of the holder within the container J.

With reference to FIGS. 6A to 8, reference number 200 designates a crimping kit according to various embodiments. In embodiments the crimping kit 200 includes a crimping instrument 201 with a crimping orifice 202 having a longitudinal axis X200, the crimping instrument being preferably mounted on a base member B, a rectilinear guide 203 oriented parallel to the longitudinal axis X200, the holder 1 with the heart valve prosthesis 100 coupled thereto.

Optionally, the crimping kit 200 may come provided with the holder 1 (with the attached prosthesis 100) in the storage kit S, so to provide a stand-alone package that can be deployed in the operational theater when necessary.

The kit 200 may also include a support post 204 for the shaft of a delivery instrument which, during crimping and loading operations of the prosthesis 100, is positioned coaxially to the axis X200 for loading of the prosthesis. The post 204 may be provided as a sliding element capable of a linear motion X204+/− in a direction parallel to the axis X200, to accommodate for different delivery instrument lengths.

The crimping kit 200 allows for a rapid, fail-safe crimping procedure of the prosthesis 100 based on the features of the holder 1.

Once the kit 200 and the holder 1 with the prosthesis 100 attached thereto have been provided, the holder 1 may be grabbed by the practitioner (or by assistant medical personnel in the operational theater) and coupled to the rectilinear guide 203. Specifically, the angular reference member 19 on the annular element 2 is mated with the rectilinear guide 203 so as to assemble a prismatic guide, wherein the angular reference member 19 (and the holder 1 as a whole, accordingly) acts as a slider, while the guide 203 acts as a guide member for the slider. The holder 1 is mated to the guide 203 so as to present the prosthesis 100 to the crimping orifice 202 of the crimping instrument 201, while the holder 1 is located in a "trailing" position relative to the prosthesis.

The holder 1 with the prosthesis 100 attached thereto may be then advanced towards the crimping orifice 202 along the guide 203 (displacement X203 in FIG. 6A) so to insert the heart valve prosthesis 100 into the crimping orifice 202, and set the armature 102 in a position that allows the same to be later contracted by crimping members of the instrument 200 (FIG. 6B), subject to removal of locking member 4. The locking member 4 is still coupled to the annular member 2 to ensure that during the whole insertion of the heart valve prosthesis 100 into the crimping orifice 202, the prosthesis does not experience undesired displacements that result in a misplacement thereof.

With the holder 1, the prosthesis 100 maintains the positioning imparted thereto at the time of coupling of the same to the holder 1. As already described, the supporting formations 3 with the coupling features or profiles 9 preventing the prosthesis 100 from axial translation, from rotation around the axis X1, as well as from radial outward expansion. In this way, the angular reference member 19 is univocally representative of the actual orientation of the prosthesis 100 around the axis X1. Once the holder 1 is mated to the guide 203, the axes X1 and X200 line up and the angular position of the prosthesis 100 becomes fully defined relative to the crimping instrument 201 (and the crimping orifice 202) as well. The angular reference member 19 thus eliminates any risk of angular misplacement of the prosthesis 100, moreover in a way that only requires a very easy operation such as mating a slider to a guide. Additionally, the provision of the locking member 4 avoids any displacement of the valve prosthesis 100 during manipulation.

Once the prosthesis 100 is fully into the crimping orifice 202, the prosthesis shall be cleared relative to the radial contraction. This is made, in various embodiments, by removal of the locking member 4 from the annular member 2 of the holder 1 (FIGS. 7A, 7B), for example by axial sliding thereof away from the annular member (e.g. in a direction opposite that of X203). Other defeat mechanisms may of course be envisaged for the locking member 4, for example the same may be provided as a variable diameter member, wherein the variation in diameter may be controlled via a push button on the locking member itself, in a way at least roughly similar to releasable joints with radially slidable studs or pins.

Removal of the locking member 4 thus removes the constraint that prevents the prosthesis 100 from being radially collapsed/contracted. Additionally, removal of the locking member 4 also clears the lumen 6 for insertion of the carrier portion of the delivery instrument, which at this point may be set on the post 204 and into the crimping orifice 202.

In embodiments, the removal of the locking member may advantageously be provided just prior to installation of the delivery instrument and subsequent crimping of the prosthesis to ensure maximum positional stability and loading of the prosthesis 100 onto the instrument, essentially to avoid any accidental misplacement of the prosthesis 100 relative to the crimping instrument 200 prior to the crimping and loading of the same onto the delivery instrument.

This is an additional safety feature of the holder 1, which essentially allows the crimping orifice to be cleared for delivery instrument insertion and crimping only when the prosthesis is firmly and correctly set in place.

Figure 8:
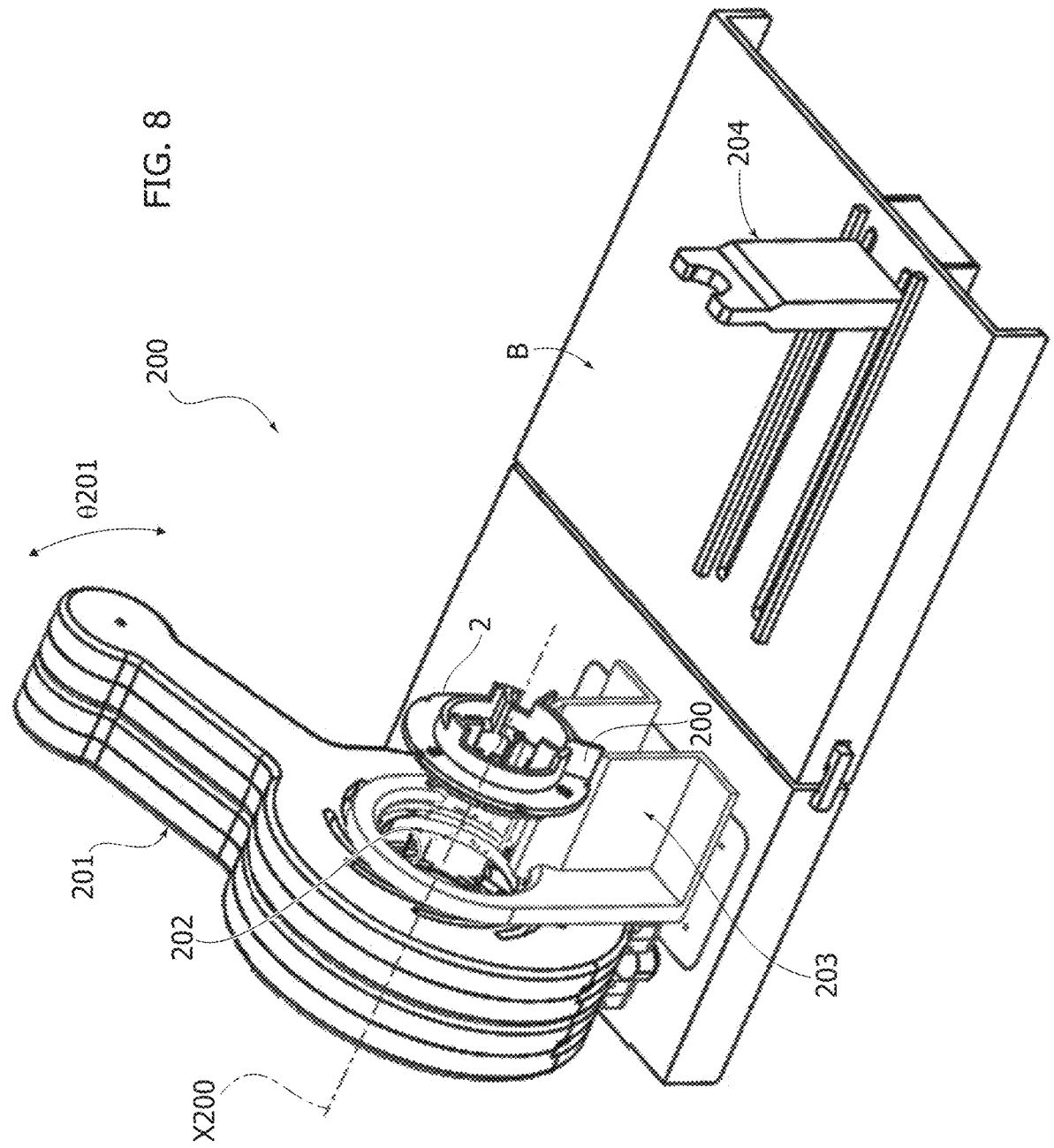

The prosthesis 100 is then crimped (e.g. by rotation of the handle of the crimping instrument 200 in the direction $\theta_{201}$ in FIG. 8) and loaded into the carrier portion of the delivery instrument. During crimping operation, the annular member 2 remains into the crimping orifice, as the same does not provide any hindrance to the crimping action, which is a radial contraction action. Instead, crimping of the heart valve prosthesis 100 results in a disengagement of the armature 102 from the supporting formations 3 due to a migration of the portion of the armature 102 received in the coupling feature or profile 9 radially inwardly and off the coupling profile itself (e.g. off the arched track 11).

The annular member 2 may then optionally be removed from the crimping instrument 200, e.g. by sliding it away from the crimping orifice 202 along the guide 203 in a direction opposite to X203, and over the delivery instrument shaft. Once the latter is lifted too away from the crimping orifice 202, the annular element 2 may then be removed from the delivery instrument shaft.

Generally, however, the annular member 2 is left in place on the guide 203 and taken away after takeoff of the delivery instrument.

While in embodiments the most advantages in terms of fail safety and ease of crimping may be provided by combining the structure of the holder 1 (annular member+ locking member) with the angular reference member 19, in certain embodiments the angular reference member 19 and the guide 203 may be dispensed with, instead relying on more conventional angular positioning techniques, for example a mating notch/pin pair on the annular member 2 and the crimping instrument 200. While still retaining all of the benefits in terms of positional stability of the prosthesis into the crimping orifice, these embodiments only perform slightly less efficiently in terms of angular positioning of the holder relative to the crimping instrument, requiring i.e. a minor manual alignment operation (e.g. a rotation until the mating notch/pin pair clicks into engagement) instead of coming already angularly positioned and ready to insert as with the holder 1 in the embodiments pictured by the figures.

Naturally, while the ideas and the principles of the disclosure remain the same, the details of construction and the embodiments may widely vary with respect to what has been described and illustrated by way of example, without departing from the scope of the present disclosure.

The invention claimed is:

1. A holder for a heart valve prosthesis comprising a radially contractible armature and a prosthetic valve carried by said armature, the holder including:
    an annular member having a longitudinal axis and comprising a plurality of supporting formations, said supporting formations protruding radially inwardly of said annular member; and
    a locking member configured for coupling with said annular member,
    wherein:
    each supporting formation includes a coupling profile configured for engaging the armature of a heart valve prosthesis, the coupling profile being configured to prevent a displacement of the armature along said longitudinal axis and being configured to prevent rotation of the armature around the longitudinal axis, while leaving the armature unconstrained in a radially inward direction, and
    the locking member is configured to removably mate with the annular member to provide a radial constraint to the armature in a radially inward direction at the supporting formations.

2. The holder of claim 1, wherein the annular member defines a lumen, the supporting formations protruding inwardly of said lumen.

3. The holder of claim 1, wherein the annular member includes an angular reference member configured for a sliding coupling with a fixed rectilinear guide, the angular reference member having a predetermined position relative to the supporting formations.

4. The holder of claim 3, wherein the angular reference member is provided on a periphery of said annular member and is configured as a slider member of a prismatic guide.

5. A crimping kit comprising:
    a crimping instrument with a crimping orifice having a longitudinal axis;
    a rectilinear guide oriented parallel to the longitudinal axis;
    a holder according to claim 3; and
    a heart valve prosthesis comprising a radially contractible armature and a prosthetic valve carried by said armature, the heart valve prosthesis being coupled to the holder at the supporting formations,
    wherein the angular reference member of the holder is slidably coupled to said rectilinear guide to provide axial insertion of the prosthetic heart valve into the crimping orifice along the longitudinal axis thereof.

6. The holder of claim 1, wherein each coupling profile is a coupling interface for an arched strut comprising:
    a cylindrical wall; and
    an arched track provided on the cylindrical wall and configured for receiving an arched strut,
    each coupling interface facing radially inwardly of said annular member, wherein at least one of said supporting formations includes a guide member for guiding said locking member upon mating to the annular member.

7. The holder of claim 6, wherein said guide member is configured for guiding said locking member in a direction parallel to said longitudinal axis.

8. The holder of claim 6, wherein said arched track includes:
   a tooth protruding from the cylindrical wall and radially inwardly of the annular member; and
   a pair of arched protrusions arranged on opposite sides of said tooth.

9. The holder of claim 8, wherein said arched protrusions are spaced from one another in correspondence of said tooth.

10. The holder of claim 1, wherein said locking member is a hub member configured for mating to the annular member coaxially to the longitudinal axis thereof and including a cylindrical portion configured to settle among the supporting formations when the locking member is mated to the annular member.

11. The holder of claim 10, wherein the locking member further includes a guide portion, particularly provided on a rim, configured for slidably coupling with the guide members of the supporting formations.

12. The holder of claim 11, wherein the guide portion is further configured to abut on an axial end portion of the supporting formations.

13. The holder of claim 1, further including the heart valve prosthesis having the radially contractible armature and the prosthetic heart valve carried by said armature, the armature including:
   an annular part; and
   a pattern of arched struts carried by said annular part, said pattern of arched struts having proximal ends connected to said annular part, and distal ends spaced axially from the proximal ends and opposite said annular part,
   wherein distal portions of the arched struts engage corresponding coupling profiles of the supporting formations.

14. The holder of claim 13, wherein the distal portions of the arched struts are received in arched tracks of the coupling profiles.

15. A holder for a heart valve prosthesis comprising a radially contractible armature and a prosthetic valve carried by said armature, the holder including:
   an annular member having a longitudinal axis and comprising a plurality of supporting formations; and
   a locking member configured for coupling with said annular member,
   wherein:
   each supporting formation includes a coupling feature configured for engaging the armature of a heart valve prosthesis, so as to prevent the displacement of the armature along said longitudinal axis and rotation of the armature around the longitudinal axis, and
   the locking member is configured to removably mate with the annular member to provide a radial constraint to the armature in a radially inward direction at the supporting formations.

16. The holder of claim 15, wherein each coupling feature provides a coupling interface for an arched strut comprising:
   a cylindrical wall; and
   an arched track provided on the cylindrical wall and configured for receiving an arched strut,
   each coupling interface facing radially inwardly of said annular member.

17. The holder of claim 15, wherein at least one of said supporting formations includes a guide member for guiding said locking member upon mating to the annular member.

18. The holder of claim 15, wherein said locking member is a hub member configured for mating to the annular member coaxially to the longitudinal axis thereof and including a cylindrical portion configured to settle among the supporting formations when the locking member is mated to the annular member.

19. The holder of claim 15, wherein the annular member includes an angular reference member configured for a sliding coupling with a fixed rectilinear guide, the angular reference member having a predetermined position relative to the supporting formations.

\* \* \* \* \*